United States Patent [19]

Romano et al.

[11] 4,062,884

[45] Dec. 13, 1977

[54] PROCESS FOR THE PREPARATION OF DIALKYLCARBONATES

[75] Inventors: Ugo Romano, Milan; Ugo Melis, S. Donato Milanese (Milan), both of Italy

[73] Assignee: ANIC, S.p.A., Palermo, Italy

[21] Appl. No.: 674,893

[22] Filed: Apr. 8, 1976

[30] Foreign Application Priority Data

Apr. 9, 1975 Italy .................................. 22143/75

[51] Int. Cl.$^2$ ...................... C07C 68/00; C07C 68/06
[52] U.S. Cl. .................................................. 260/463
[58] Field of Search ......................................... 260/463

[56] References Cited

U.S. PATENT DOCUMENTS 3,248,414  4/1966  Stevens ................................ 260/463

3,642,858  2/1972  Frevel et al. ......................... 260/463

FOREIGN PATENT DOCUMENTS 4,975,516  9/1972  Japan .................................. 260/463

Primary Examiner—Delbert R. Phillips
Attorney, Agent, or Firm—Morgan, Finnegan, Pine, Foley & Lee

[57] ABSTRACT

A process for the preparation of dialkylcarbonates by reacting an alcohol with a cyclic carbonate, wherein the reaction is carried out in the presence of an organic base, preferably a tertiary aliphatic amine, at a temperature of between 50° and 150° C and at a pressure of between 0.1 and 10 kg./sq.cm., the conversion of dialkylcarbonate being selective and avoiding the need of removing inorganic by-products.

6 Claims, No Drawings

PROCESS FOR THE PREPARATION OF DIALKYLCARBONATES

The present invention relates to a process for the synthesis of dialkylcarbonates, starting from alcohols and from a cyclic carbonate, having the formula:

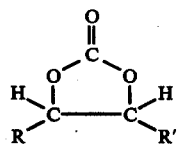

wherein R and R' represent hydrogen, alkyl or alkoxy, which are reacted in the presence of organic bases.

It is known that alkyl carbonates of the type ROCOOR can be obtained from alcohols and cyclic carbonates corresponding to the above formula through a transesterification reaction in the presence of alkali alcoholates or hydrates; however, moderate amounts of inorganic compounds are produced by these reactions, which must be removed by methods which, sometimes, may unfavourably affect the general economy of the process.

It has now been found that dialkylcarbonates can be prepared by reacting alcohols with cyclic carbonates in the presence of organic bases, according to a process which is undoubtedly advantageous with respect to the known processes, since no removal of inorganic compounds is needed and the catalysts can be totally recovered by means of a simple distillation. Alternatively, the same bases can be utilized in form of a polymer, thus affording the possibility of separating the catalysts from the reaction mixture by filtration or, more simply, by using a fixed or fluidized catalyst bed.

The reactants are fed to the reaction according to mole ratio which is indifferently variable, even if an alcohol excess is preferable; as regards the organic base, which is preferably a tertiary aliphatic amine, an amount is used varying between 0.1 and 20% by weight referred to the reaction mixture.

The reaction temperature is generally varying between 50° and 150° C., whereas the pressure is maintained at a value of between 0.1 and 10 kg/sq.cm.

All the operating details will be more evident from the following illustrative Examples, which, however, should not be construed in limitative sense as regards the invention.

EXAMPLE 1

In a 500 ml flask, bearing overhead a 30 tray distillation column, 200 mls of methanol, 20 g of ethylene carbonate and 2 mls of triethylamine were charged at 70° C.

By continuously distilling the methanol-dimethylcarbonate azeotrope with a refluxing ratio of 10/1 during 3 hours, the almost complete conversion of the ethylene carbonate was obtained, with a total selectivity to ethylene glycol and dimethylcarbonate.

EXAMPLE 2

In the same apparatus of Example 1, 200 mls of methanol, 30 g of propylene carbonate and 2.15 g of dimethylbenzylamine were charged.

At a temperature of 70° C and for a time of 5 hours, with a refluxing ratio of 20/1, the complete conversion of the propylene carbonate to glycol was obtained with a total selectivity to dimethyl-carbonate.

EXAMPLE 3

200 mls of methanol, 20 g of ethylene carbonate and 1.85 mls of triethanolamine were charged in the same apparatus of the Example 1. At a temperature of 70° C and for a time of 4 hours, with a refluxing ratio of 15/1, the almost complete conversion of the ethylene carbonate to dimethylcarbonate was obtained.

EXAMPLE 4

50 g of ethylene carbonate and 50 mls of ethanol together with 3.4 mls of tributylamine were charged in a 250 ml flask at 95° C.

The vapours, containing 15% of ethylene carbonate and 85% of ethanol, were condensed and fed to a distillation column, ethanol being removed overhead and recycled to the reactor, whereas diethylcarbonate was removed as the bottom product. During 4 hours the ethylene carbonate was completely converted with total selectivity to diethylcarbonate.

EXAMPLE 5

200 mls of methanol, 20 g of ethylcarbonate and 2 g of a basic resin (XE 295, sold by ROHM & HAAS, with tertiary aliphatic amine groups), were charged in the apparatus of the Example 1.

At 70° C and during 6 hours, with a refluxing ratio of 20/1, 83% of the ethylcarbonate was converted with a total selectivity to glycol and dimethylcarbonate.

We claim:

1. A process for the preparation of a dialkylcarbonate, which consists in reacting an alcohol with a cyclic carbonate having the formula:

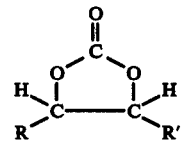

in which R and R' represent hydrogen, alkyl or alkoxy, in the in the presence of a catalyst consisting of a tertiary aliphatic amine in the temperature range of from 50° to 150° C and in the pressure of from 0.1 to 10 kg/cm².

2. A process for the preparation of a dialkylcarbonate as claimed in claim 1, characterized in that the reaction is carried out in the presence of an amount of catalyst in the range between 0.1 and 20% by weight referred to the feed.

3. A process as defined in claim 1 wherein the tertiary aliphatic amine is triethylamine.

4. A process as defined in claim 1 wherein the tertiary aliphatic amine is dimethylbenzylamine.

5. A process as defined in claim 1 wherein the tertiary aliphatic amine in triethanolamine.

6. A process as defined in claim 1 wherein the tertiary aliphatic amine is tributylamine.

* * * * *